United States Patent

Lund

[11] Patent Number: 5,996,417
[45] Date of Patent: Dec. 7, 1999

[54] PRELOAD PISTON ACTUATOR

[75] Inventor: Douglas A. Lund, Anacortis, Wash.

[73] Assignee: Team Corporation, Burlington, Wash.

[21] Appl. No.: 09/046,058

[22] Filed: Mar. 23, 1998

[51] Int. Cl.⁶ .................................................. G01M 3/32
[52] U.S. Cl. ................................................ 73/662; 73/665
[58] Field of Search ........................... 73/665, 662, 663,
73/668, 71.6; 91/422

[56] References Cited

U.S. PATENT DOCUMENTS

| | | | |
|---|---|---|---|
| 3,811,364 | 5/1974 | Harkrader | 91/422 |
| 4,350,053 | 9/1982 | Folger | 74/2 |
| 4,568,058 | 2/1986 | Shelton | 251/62 |
| 4,602,555 | 7/1986 | Bushey | 92/61 |
| 4,893,857 | 1/1990 | Bobinger et al. | 293/136 |
| 4,949,540 | 8/1990 | Wich | 60/387 |
| 5,216,931 | 6/1993 | Hirsch et al. | 74/477 |
| 5,343,752 | 9/1994 | Woyski et al. | 73/665 |
| 5,488,895 | 2/1996 | Tobiasz | 91/519 |
| 5,522,421 | 6/1996 | Holt et al. | 137/505.22 |
| 5,544,528 | 8/1996 | Woyski et al. | 73/665 |

*Primary Examiner*—Hezron Williams
*Assistant Examiner*—Thuy Vinh Tran
*Attorney, Agent, or Firm*—Christie, Parker & Hale, LLP

[57] ABSTRACT

A hydraulic actuator for vibration testing equipment includes a double-acting piston having a coaxial floating piston assembly coupled to one end of the piston rod. The floating piston assembly has a preload piston pressurized to allow the overall length of the actuator to adjust for small changes in distance between the mating surfaces of the vibration test equipment when the equipment tilts or rotates.

20 Claims, 6 Drawing Sheets

PRELOAD PISTON ACTUATOR

FIELD OF THE INVENTION

The present invention relates generally to hydraulic actuators for vibration testing equipment, and more particularly to a double-acting piston actuator having a floating piston assembly positioned at one end of a piston rod.

BACKGROUND OF THE INVENTION

Various methods and systems have been adopted in the vibration testing industry to simulate vibration and shock environments. There is a wide range of potential uses for such methods and systems, from earthquake simulators to the development of vibration-tolerant product designs. For example, a number of industries use vibration testing for determining their products' effectiveness and longevity when subjected to these environmental extremes. Vibration testing may be conducted to verify that a specific design will survive in its intended vibration environment, or to screen out defective parts at an early stage in the manufacturing process.

Vibration testing has traditionally been done with the test article restrained to move in a single axis. However, it has been shown that vibration testing in three mutually exclusive axes simultaneously can simulate real world conditions better than single axis testing. Therefore, to better simulate real world conditions, it is often desirable to use multiple-axis, multiple degree-of-freedom vibration test fixtures.

One such multiple-axis, multiple-degree-of-freedom vibration test fixture is disclosed in U.S. Pat. No. 5,343,752 to Woyski et al., and illustrated herein as FIGS. 1 and 2. The fixture 10 includes a normally horizontal upper fixture base 12, supported by three sets of upwardly extending pairs of rigid support arms 14, 16, 18. The support arms are mounted to a rigid stationary lower base 20 so as to accommodate vibration motion of the upper base in both the vertical plane and the horizontal plane. A hydraulic vibration actuator module 22 is affixed to each support arm, each module having a double-acting piston actuator assembly 24 reciprocating along a horizontal axis and a double-acting piston actuator assembly 26 reciprocating along a vertical axis. This permits the vibration table to be vibrated along orthogonal x and y-axes and rotated with a z-axis rotation in the horizontal plane by corresponding combinations of vibration of the three horizontal piston actuator assemblies. Separately, components of vertical forces are induced by the three sets of vertical piston actuator assemblies to oscillate the table in various combinations of pitch, yaw or heave orientations in the vertical plane, combined with horizontal plane movement.

Each of the hydraulic piston actuator assemblies has a split-piston design, wherein a pair of pistons are aligned along a common axis of vibration, and opposite end portions of the pistons project outwardly from opposite sides of the actuator housing. The pistons each reciprocate in a corresponding cylinder contained internally within the actuator housing as hydraulic fluid acts on ends of the pistons.

Although the split-piston actuator design has certain advantages, it has been found that there are some disadvantages associated with this design, especially in longer stroke applications (i.e. greater than 4 inches). Longer strokes often create higher side or bending loads on the actuator when used in multi-degree of freedom machines. Various features of the split-piston actuator design result in relatively poor side load capability in the longer stroke applications. For example, in order to accommodate such longer strokes, the overall length of the actuator must be increased, and the side loads on the actuator become extremely difficult to handle. Additionally, the split-piston actuator design does not allow the piston rod diameter to be changed in order to improve the side load capability of the actuator. Since the hydraulic fluid acts on one end of the piston rod, the diameter of the piston rod is determined by the required actuator force. Moreover, the bearings supporting each of the pistons in the split-piston actuator design are relatively close together, thus intensifying the existing problems associated with the side load capability of the actuator.

Consequently, a need exists for an improved hydraulic vibration actuator capable of addressing the disadvantages associated with the prior art actuator designs identified above. More specifically, a need exists for a hydraulic vibration actuator having increased side load capability for use in long stroke vibration testing applications.

SUMMARY OF THE INVENTION

The present invention, therefore, provides an improved hydraulic actuator designed to minimize the disadvantages associated with the prior art actuator designs, particularly those arising when used in vibration test equipment requiring a long stroke capability. The hydraulic actuator according to the present invention includes a central actuator housing having a bore extending through the housing. A primary piston is provided within the bore, for reciprocating movement therein. The movement of the primary piston is controlled by a hydraulic servo valve. On one end of the primary piston, a floating piston assembly is provided. The floating piston assembly includes a preload piston, axially aligned with the primary piston. The preload piston has an effective piston area greater than the effective piston area of the primary piston. Hydraulic fluid from the servo valve pressurizes the preload piston to allow the overall length of the actuator to adjust for small changes in distance between the mating surfaces of a structure when the structure tilts or rotates with respect to the actuator centerline. Additionally, pad bearings are provided on opposite ends of the actuator to transfer reciprocating motion of the primary piston into vibrational motion of a test fixture when the actuator is mounted between mating surfaces of the fixture. One pad bearing is coupled to one end of the primary piston and another pad bearing is coupled to one end of the preload piston.

In one embodiment, a preload piston having a smaller diameter than the actuator rod is located within a bore at one end of the primary piston. Alternatively, a separate housing may be coupled to one end of the primary piston, with the preload piston reciprocatingly provided within a bore of the housing, extending into the housing from one end thereof.

BRIEF DESCRIPTION OF THE DRAWINGS

These and other features and advantages of the present invention will be appreciated as the same become better understood by reference to the following Detailed Description when considered in connection with the accompanying drawings, wherein.

DETAILED DESCRIPTION OF THE INVENTION

Figure 1:
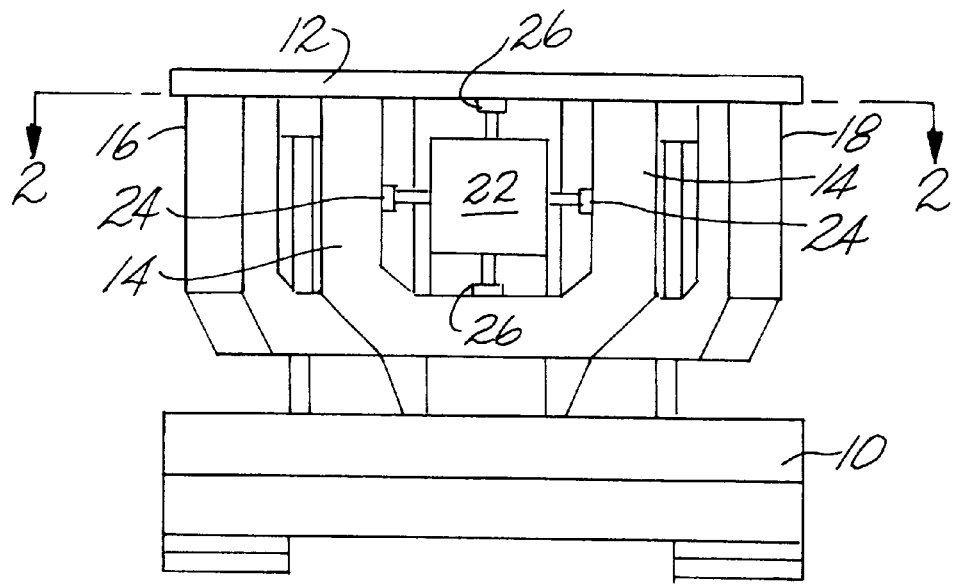
FIG. 1 is a semi-schematic front elevation view of a prior art multiple-axis, multiple degree-of-freedom vibration test fixture using a split-piston actuator design.
Figure 2:
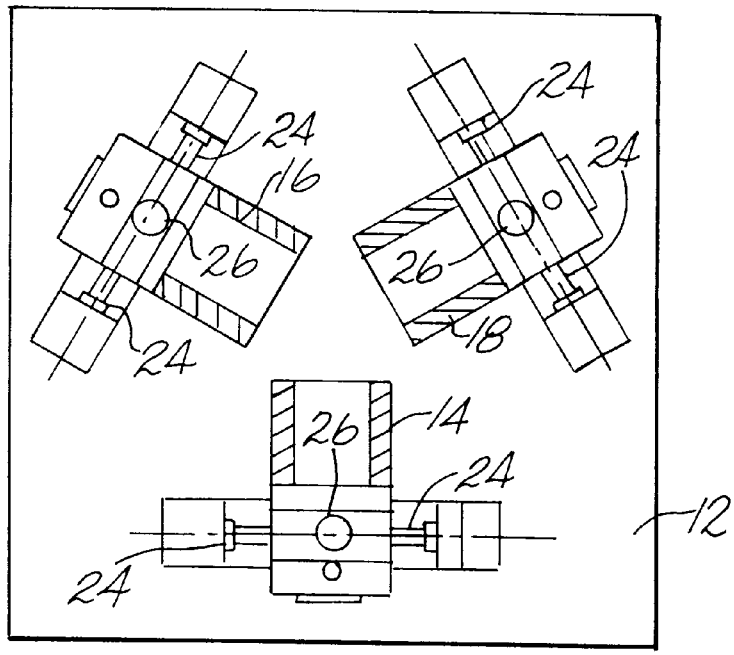
FIG. 2 is a semi-schematic top view taken along line 2—2 of FIG. 1.
Figure 3:
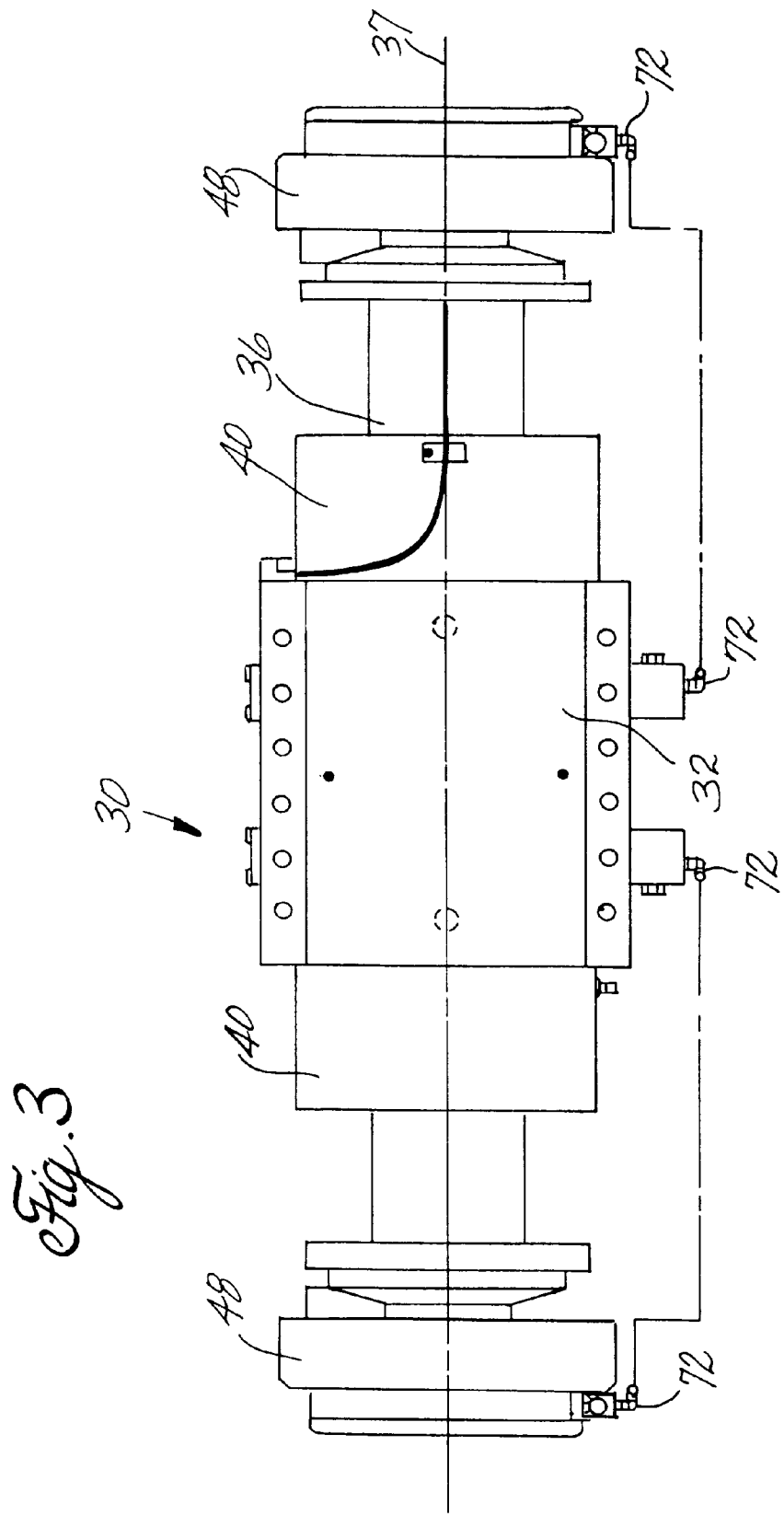
FIG. 3 is a top elevation view of an embodiment of a hydraulic actuator according to the present invention.
Figure 4:
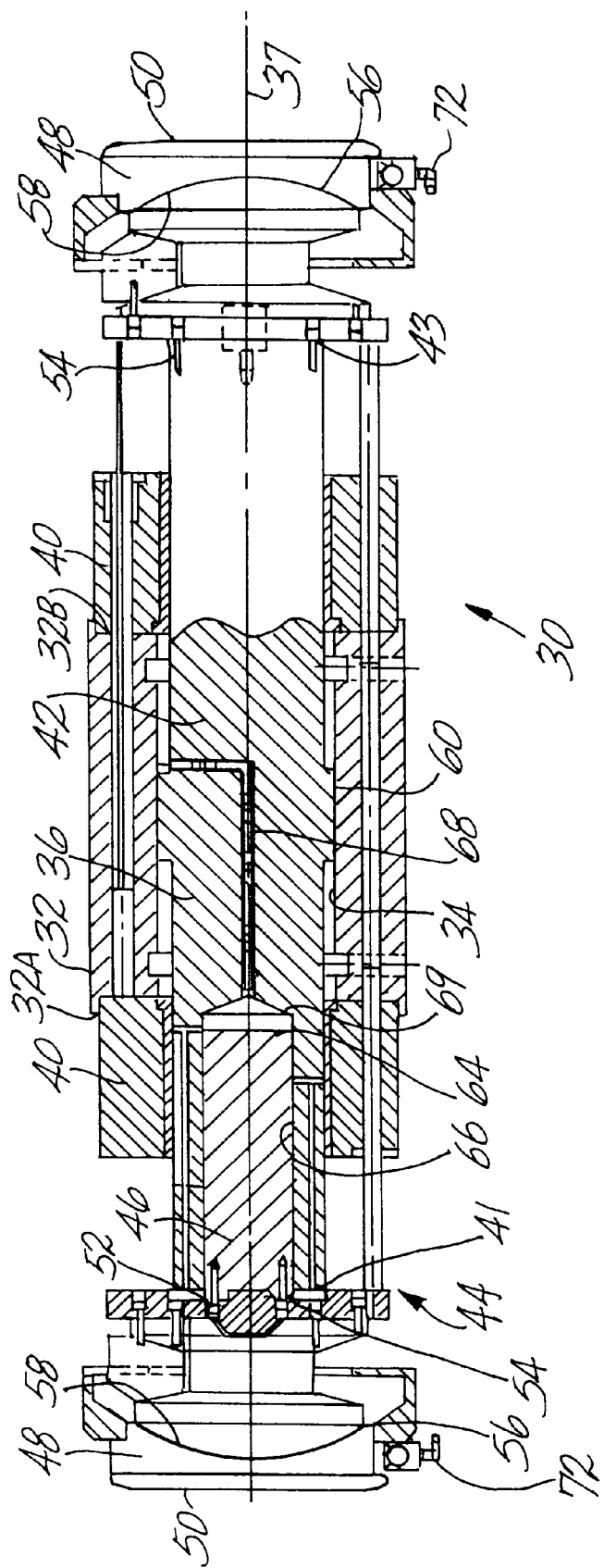
FIG. 4 is a partial cross-sectional side elevation view of the hydraulic actuator of FIG. 3.

Referring now to FIGS. 3 and 4, one embodiment of the hydraulic piston actuator 30 according to the present invention is illustrated. The actuator 30 generally includes a central housing 32 having a bore 34 extending through the housing, a double-acting primary piston 36 located within the bore for reciprocating motion therein, and a hydraulic servo valve 38 (FIG. 6) attached to the housing 32 for controlling the movement of the primary piston 36 along axis 37. A pair of bearings 40 are used to support the reciprocating motion of the primary piston 36 and are aligned with, and coupled to, the housing at sides 32A, 32B. The primary piston 36 includes an actuator rod 42 having a pair of opposed ends 41, 43 extending outwardly from opposite sides 32A, 32B of the central housing bearings 40. A floating piston assembly 44, having a preload piston 46, is provided at end 41 of the actuator rod 42. However, the preload piston 46 has an effective area that is greater than the effective area of the primary piston 36. For example, the preload piston 46 may have an effective area of approximately 12.57 square inches and the primary piston 36 an effective area of approximately 11.25 square inches for a dynamic stroke of approximately 10 inches.

Figure 7:
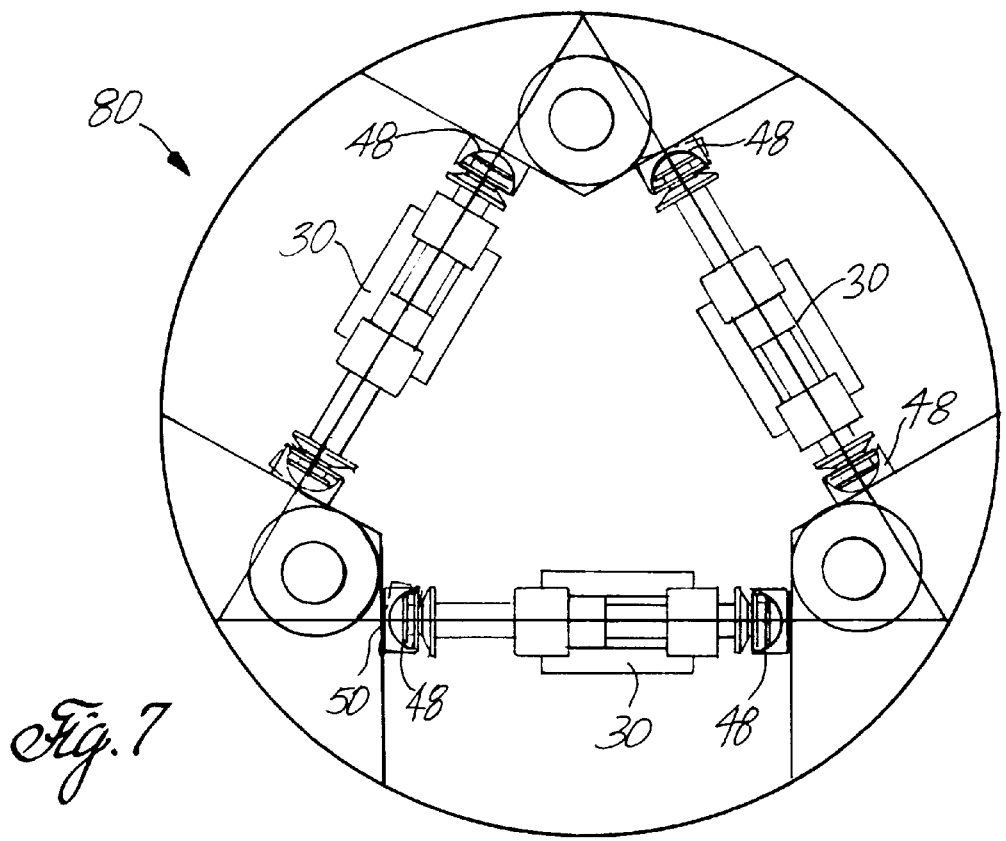
FIG. 7 is a semi-schematic top elevation view of a multiple degree-of-freedom vibration test fixture using the hydraulic actuator of FIG. 3.

A pair of pad bearings 48 are located on opposite ends of the actuator 30. When the actuator is installed in a vibration test fixture, an outer surface 50 of each pad bearing 48 engages a rigid mating surface of the vibration test fixture support system to transfer the reciprocating motion of the actuator to the test fixture (FIG. 7). One of the pad bearings is coupled to end 43 of the actuator rod and the other pad bearing is coupled to an end 52 of the preload piston 46. The pad bearings 48 may be coupled to the actuator rod by any means well known in the art, such as with fasteners 54.

In a presently preferred embodiment, pad bearings 48 are self-aligning pad bearings, which include a convex spherical end 56 and a mating concave spherical cup 58. The spherical ends 56 of the pad bearings are free to slide or rotate relative to the spherical cups 58, which provides the self-aligning feature of the pad bearings.

The primary piston 36 includes a shoulder 60 on the actuator rod 42. The shoulder 60 is substantially centrally located along the actuator rod 42, and defines the effective piston area of the primary piston against which hydraulic fluid will act during operation of the actuator. As can be seen from FIG. 4, in a presently preferred embodiment, the shoulder 60 is an annular ring around the actuator rod 42 that is coupled to or machined into the actuator rod 42.

When compared with the prior art split-piston actuator designs, the actuator 30 significantly reduces the overall length of the actuator assembly and increases the sideload capability of the actuator. For example, for a seven (7) inch stroke actuator, a split-piston actuator would have an overall length of about sixty-seven and a half (67.5) inches. In an exemplary embodiment of a hydraulic actuator according to the present invention having the same stroke capability, the overall length of the actuator is only about forty-five (45) inches, resulting in a more compact actuator assembly.

Additionally, as discussed above, longer strokes often create higher side loads on the actuator when used in multiple degree-of-freedom text fixtures. To handle the increased side loads, a larger actuator rod diameter is desirable. The hydraulic actuator provided by the present invention permits the actuator rod diameter to be increased as needed to handle the side load requirements, without affecting the effective piston area of the primary piston or the resulting force that the actuator will produce. The effective piston area of the primary piston is defined by the shoulder 60, and thus can be established independent of the rod diameter to provide the desired actuator force. In prior art split-piston actuator designs, the effective piston area is determined by the rod diameter as the hydraulic fluid acts against one end of the piston rod. Thus, the rod diameter cannot be varied independently of the effective piston area to accommodate the increased side load requirements.

Moreover, the support bearings 40 of the actuator 30 are farther apart than the respective bearings utilized in the prior art split-piston actuator design, which further improves the side load capability of the actuator.

Figure 6:
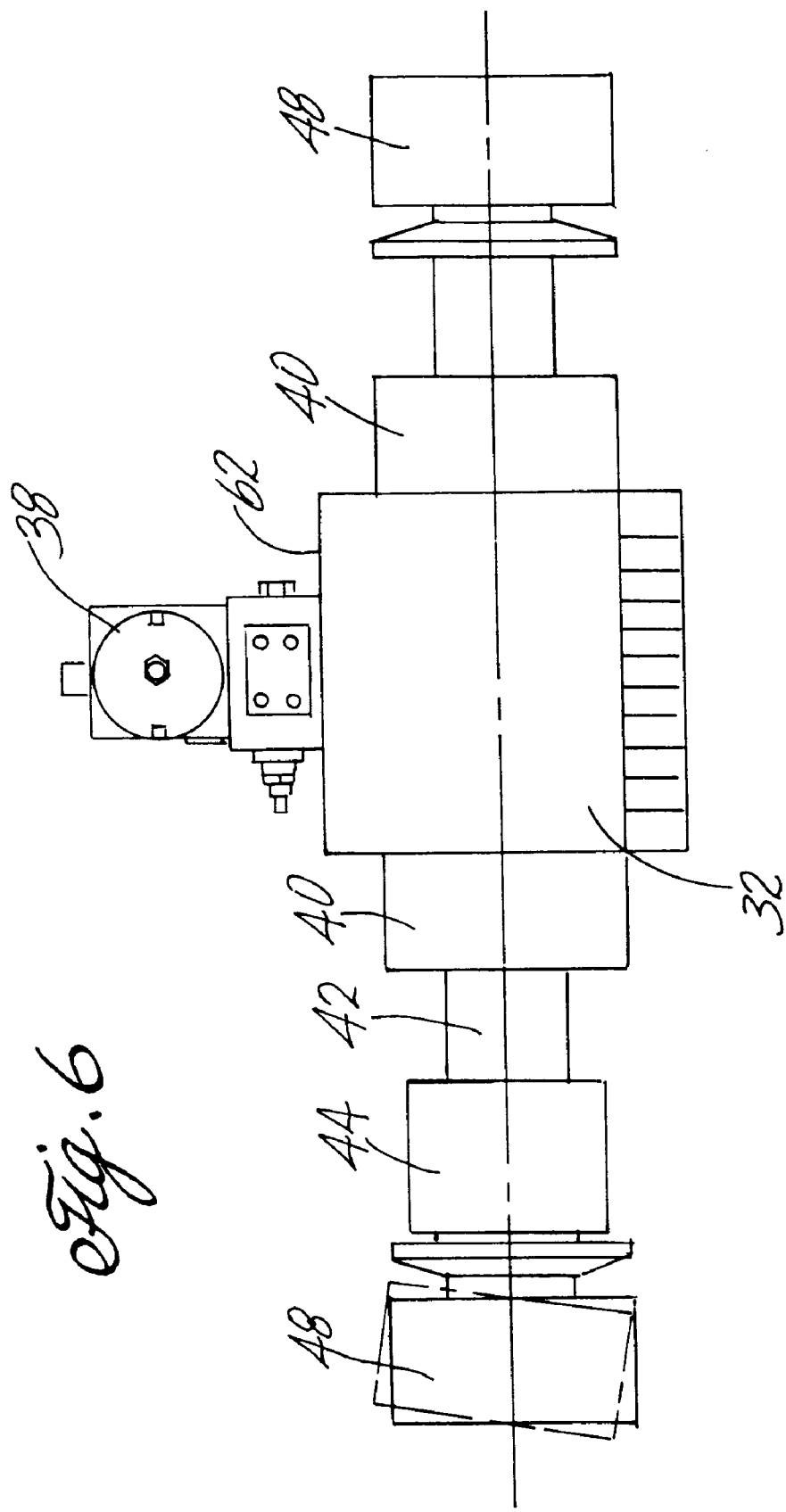
FIG. 6 is a side elevation view of the hydraulic actuator of FIG. 5 with an externally mounted hydraulic servo valve.

Referring now to FIG. 6, the hydraulic servo valve 38 is illustrated mounted to an outer surface 62 of the actuator central housing 32. The hydraulic servo valve 38 controls primary piston movement by producing a controllable frequency input for inducing vibration motion directly to the piston. As illustrated, the hydraulic servo valve 38 includes a pilot valve 39, such as a V20 pilot valve which controls a slave valve 41, such as a V140 slave valve. Hydraulic fluid flows from the servo valve 38 into the bore 34 of the actuator housing, and alternatively acts on opposite sides 60A, 60B of the shoulder 60 to reciprocate or vibrate the primary piston 36 at the frequency set by the input of the servo valve 38.

One of the advantages of the external mounting of the servo valve 38 is that the servo valve can be removed and installed without disturbing the actuator housing and piston assembly. This is not possible in a split-piston actuator design where the servo valve assembly is an integral part of the actuator housing and piston assembly.

Additionally, the external mounting of the servo valve does not significantly affect the actuator's performance capability. Hydraulic fluid is a compressible substance, and thus the hydraulic stiffness of an actuator is affected by the total trapped volume of hydraulic fluid between the servo valve and the piston. Minimizing this volume is desirable for improving the high frequency response of the actuator. By providing an integral servo valve in the actuator housing, the prior art split-piston design effectively minimized the total trapped volume of hydraulic fluid by reducing the distance between the servo valve and the piston. External mounting of the servo valve will produce some additional trapped volume of hydraulic fluid due to the relative position between the external servo valve and the piston, however, in longer stroke applications, the additional trapped volume becomes a smaller percentage of the total trapped volume, and therefore does not significantly affect the actuator's high frequency response capabilities.

As shown in FIG. 4, the floating piston assembly 44 includes a preload piston 46, coaxial with the primary piston 36, which allows the overall length of the actuator 30 to adjust for small changes in distance between the mating surfaces of a structure when the structure tilts or rotates with respect to the actuator centerline 37. This is necessary to maintain constant contact between the outer surfaces 50 of the pad bearings 48 and the respective mating surfaces of the vibration test fixture support system.

During operation of the hydraulic actuator, the preload piston 46 is constantly under hydraulic pressure to automatically extend or retract as needed to adjust to overall length of the actuator 30. The preload piston 46 is preferably pressurized by the hydraulic fluid from the servo valve 38 which drives the primary piston 36, although an external supply can alternatively be used if desired. The hydraulic fluid acts on an effective piston area of the preload piston, which must be larger than the effective piston area of the primary piston. If the effective area of the preload piston is smaller than the effective area of the primary piston, then the pad bearings will not maintain proper content with their mating surfaces. As can be further seen in FIG. 4, the hydraulic fluid acts on an end 64 of the preload piston 46, and thus, end 64 defines the effective piston area of the preload piston.

In the embodiment illustrated in FIGS. 3 and 4, the preload piston 46 has a smaller diameter than the actuator rod 42, and is located coaxially within the end 41 of the actuator rod 42. A bore 66 extends into the actuator rod 42 from end 41, and the preload piston 46 is provided in the bore 66 for reciprocating movement therein. The characteristics of the preload piston are dictated, in part, by the side load requirements of the system. Additionally, the preload piston assembly is preferably designed to allow smooth movement of the piston within the bore.

An internal port or passageway 68 is provided through the primary piston 36 between the bore 34 of the central housing 32 and the bore 66 in the primary piston 36. Hydraulic fluid from the servo valve 38 travels from the bore 34, through the passageway 68 and enters the bore 66 at an end 69, behind the end 64 of the preload piston 46 to pressurize the preload piston. Additional internal ports 70 (FIG. 5) may be provided through the primary piston 36 to carry hydraulic fluid from the servo valve 38 to the pad bearings 48 as needed. Alternatively, external ports 72 may be provided on the actuator housing 32 and pad bearings 48 so that suitable lines may be attached between the external ports to carry hydraulic fluid from the servo valve to the pad bearings.

Figure 5:
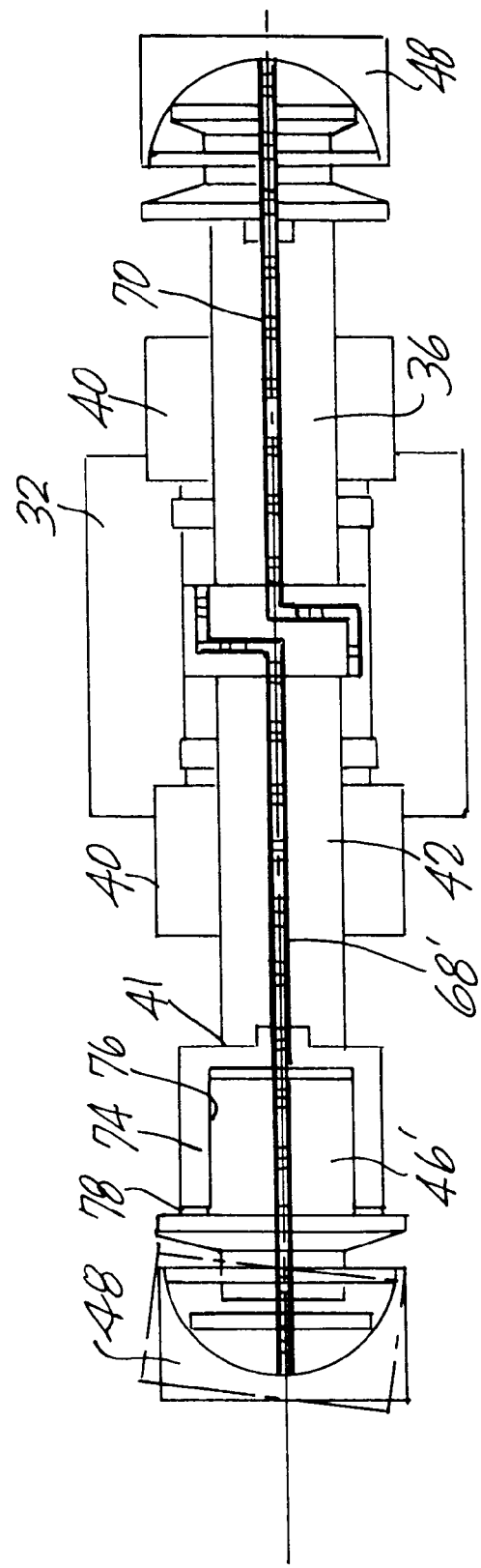
FIG. 5 is a cross-sectional side elevation view of an alternate embodiment of the hydraulic actuator according to the present invention.

An alternate embodiment of the floating piston assembly 44 is illustrated in FIG. 5. In this embodiment, a separate housing 74 for the preload piston 46' is coupled to the end 41 of the actuator rod 42. The housing includes a bore 76 extending into the housing 74 from one end 78 of the housing, and the preload piston 46' is provided within the bore 76 for reciprocating motion therein. The operation of the preload piston 46' is substantially identical to the operation of the preload piston 46 described in connection with the previous embodiment of the floating piston assembly. Similar to the previous embodiment, the effective area of the preload piston 46' is greater than the effective area of the primary piston 36'. For example, the preload piston 46' may have an effective area of approximately 16.62 square inches and the primary piston 36' an effective area of approximately 15.7 square inches for a total stroke of approximately 7.0 inches.

In the embodiment illustrated in FIG. 5, internal passageway 68' carries hydraulic fluid from the servo valve to the floating piston assembly to pressurize the preload piston. The passageway 68' continues through the preload piston 46' and the pad bearing 48 to provide hydraulic fluid from the servo valve as needed.

Figure 8:
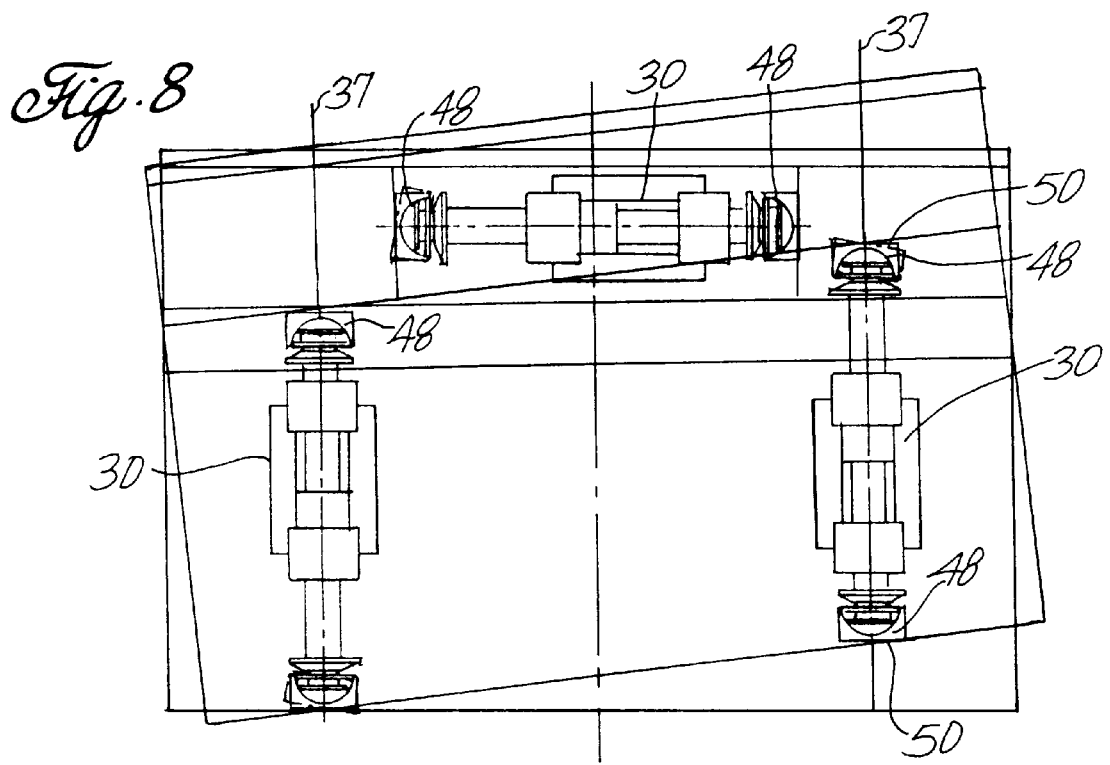
FIG. 8 is a semi-schematic side elevation view of the vibration test fixture of FIG. 7

FIGS. 7 and 8 schematically illustrate a multiple-axis, multiple degree-of-freedom vibration test fixture 80 utilizing the hydraulic actuator 30 according to the present invention. The vibration test fixture illustrated in these figures is a 6-degree of freedom machine. The text fixture 80 has a generally cylindrical housing that is driven by six hydraulic actuators 30, which give it the required motion capability. The floating piston assembly of each hydraulic actuator allows the overall length of the actuator 30 to adjust for small changes in distance between the mating surfaces of cylindrical housing when the test fixture tilts or rotates with respect to the actuator centerline 37. Thus the outer surfaces 50 of the pad bearings 48 remain in constant contact with a respective mating surface of the vibration test fixture support system.

While various embodiments of this invention have been shown and described, it would be apparent to those skilled in the art that many more modifications are possible without departing from the inventive concept herein. For example, although the floating piston assembly is illustrated and described as being on one end of the actuator, it may alternatively be positioned on either end of the actuator. It is, therefore, to be understood that, within the scope of the appended claims, this invention may be practiced otherwise than as specifically described.

What is claimed is:

1. A hydraulic actuator for use in vibration test equipment, the actuator comprising:

a central housing having a primary bore extending along an axis through the housing;

a primary piston having an actuator rod extending between opposing ends and a radially outwardly extending shoulder positioned between the piston ends to define a first effective piston area, the primary piston positioned along the axis within the primary bore for reciprocating motion therein; and a floating piston assembly coupled to one end of the primary piston, the floating piston assembly having a preload piston axially aligned with the primary piston and defining a second effective piston area, wherein the second effective piston area is greater than the first effective piston area.

2. The hydraulic actuator according to claim 1, and further comprising a hydraulic servo valve operatively coupled to the primary bore for controlling movement of the primary piston within the primary bore.

3. The hydraulic actuator according to claim 1, and further comprising a pair of pad bearings at opposite ends of the actuator, one pad bearing being coupled to an end of the preload piston and the other pad bearing coupled to the end of the primary piston opposite the floating piston assembly.

4. The hydraulic actuator according to claim 1, and further comprising a pair of support bearings coupled to and aligned with opposite ends of the central housing such that each end of the primary piston extends through one of the support bearings.

5. The hydraulic actuator according to claim 1 wherein the primary piston comprises a constant diameter actuator rod having a larger diameter shoulder to define annular first effective piston areas on opposing sides of the shoulder.

6. The hydraulic actuator according to claim 1 wherein the preload piston comprises a first end which defines the second effective piston area.

7. The hydraulic actuator according to claim 1 wherein the floating piston assembly comprises an axially aligned preload bore extending into one end of the actuator rod of the primary piston, and wherein the preload piston is positioned within the preload bore for reciprocating motion therein.

8. The hydraulic actuator according to claim 1 wherein the floating piston assembly comprises a preload housing coupled to one end of the primary piston, the preload housing having a preload bore axially aligned with the primary piston and wherein the preload piston is positioned within the preload bore for axial reciprocating motion therein.

9. The hydraulic actuator according to claim 8 wherein the preload piston is actuated by a hydraulic fluid directed from the hydraulic servo valve.

10. The hydraulic actuator according to claim 9 wherein the primary piston further comprises an internal passageway from the primary bore to the floating piston assembly, for carrying hydraulic fluid from hydraulic servo valve to the preload bore.

11. A hydraulic actuator comprising:
   a central housing having a primary bore extending along a first axis;
   a hydraulic servo valve fluidly coupled to the primary bore;
   a primary piston having a shoulder portion with a pair of outwardly extending actuator rods, each of the rods extending along the first axis from an opposing side of the shoulder, the shoulder extending radially outwardly from the actuator rods to define an annular effective area on either side of the shoulder relative to the actuator rods and against which hydraulic fluid from the servo valve acts to reciprocally drive the primary piston within the primary bore; and
   a preload piston coupled to one end of the primary piston and axially aligned with the primary piston, the preload piston defining a second effective piston area which is larger than either of the annular effective piston areas, and against which hydraulic fluid from the servo valve acts, pressurizing the preload piston to allow for adjustment of a length of the actuator.

12. The hydraulic actuator according to claim 11, and further comprising a pair of pad bearings at opposite ends of the actuator, one pad bearing coupled an end of the preload piston and the other pad bearing coupled to the end of the primary piston opposite the floating piston assembly.

13. The hydraulic actuator according to claim 11, and further comprising a pair of support bearings coupled to and aligned with opposite ends of the central housing such that each actuator rod extends through one of the support bearings.

14. The hydraulic actuator according to claim 11 wherein the actuator rods and the shoulder are an integral piece and wherein each of the annular effective areas is substantially the same.

15. The hydraulic actuator according to claim 11 wherein the preload piston comprises a first end which defines the second effective piston area.

16. The hydraulic actuator according to claim 11 wherein the floating piston assembly comprises an axially aligned preload bore extending into an end of one of the actuator rods of the primary piston and wherein the preload piston is positioned within the preload bore for reciprocating motion therein.

17. The hydraulic actuator according to claim 11 wherein the floating piston assembly comprises a preload housing coupled to one end of the primary piston, the preload housing having a preload bore axially aligned with the primary piston and wherein the preload piston is positioned within the preload bore for axial reciprocating motion therein.

18. A hydraulic actuator for use in vibration testing equipment, the hydraulic actuator comprising:
   a central housing having a primary bore extending along a first axis between a pair of opposing sides;
   a pair of support bearings, each bearing being coupled to one of the sides of the central housing;
   a hydraulic servo valve externally mounted on the central housing;
   a primary piston having a cylindrical shoulder portion with a pair of outwardly extending actuator rods, each of the actuator rods extending along the first axis from an opposing side of the axially aligned shoulder, the shoulder extending radially outwardly from the actuator rods to define an annular effective area on either side of the shoulder relative to the actuator rods and against which hydraulic fluid from the servo valve acts to reciprocally drive the primary piston within the primary bore, each of the actuator rods extending outwardly from the central housing and through a respective one of the support bearings; and
   a floating piston assembly coupled to one end of the primary piston, the floating piston assembly having a pressurized preload piston axially aligned with the primary piston, wherein the preload piston has an end defining a second effective piston area which is greater than the annular effective piston area of the primary piston and wherein the pressurized preload piston allows for adjustment of a length of the actuator; and
   a pair of pad bearings on opposite ends of the actuator, one pad bearing being coupled to an end of the actuator rod and the other pad bearing being coupled to an end of the preload piston opposite the second effective piston area.

19. The hydraulic actuator according to claim 18 wherein the primary piston comprises a passageway between the bore in the central housing and the end of the primary piston adjacent the second effective piston area, the passageway for transferring hydraulic fluid between the floating piston assembly and the hydraulic servo valve.

20. The hydraulic actuator according to claim 18 wherein the floating piston assembly comprises a cylindrical preload piston that is slidable supported within an open bore extending axially inwardly into an end of one of the actuator rods, the floating piston assembly adapted to adjust for variations in required piston stroke.

* * * * *